United States Patent [19]

Bodart

[11] 4,073,623
[45] Feb. 14, 1978

[54] ANALYTICAL DETERMINATION OF SUBSTANCES IN SOLUTION

[75] Inventor: Detlef Eugen Bodart, Darmstadt, Germany

[73] Assignee: Merck Patent Gesellschaft mit beschrankter Haftung, Darmstadt, Germany

[21] Appl. No.: 734,107

[22] Filed: Oct. 20, 1976

[30] Foreign Application Priority Data

Oct. 31, 1975 Germany .............................. 2548728

[51] Int. Cl.² .......................... G01J 3/52; G01N 21/02
[52] U.S. Cl. ...................................... 23/259; 356/191
[58] Field of Search .................. 23/259; 356/191, 192, 356/193, 194, 243

[56] References Cited

U.S. PATENT DOCUMENTS 3,520,626   7/1970   Hach .................................... 356/243

Primary Examiner—Robert M. Reese
Attorney, Agent, or Firm—Millen & White

[57] ABSTRACT

A device for supporting sample-containing tubes in generally vertical parallel adjacency, one of the tubes containing an unknown sample and the other containing a reference or comparison sample, with the bottoms of the tubes located in predetermined relationship with a color table or chart having colored or shaded portions preselected and calibrated in accordance with the particular comparison to be made, the table or chart being movable at a right angle relative to the tubes such as to provide visual comparison between the samples based on color or optical density.

7 Claims, 2 Drawing Figures

ANALYTICAL DETERMINATION OF SUBSTANCES IN SOLUTION

BACKGROUND OF THE INVENTION

Semi-quantitative analytical measurement processes of optical colorimetry are based upon the visual measurement of colorations which are formed in solutions by the addition of certain reagents. Depending upon the color reaction and the measurement range, the solutions can be of very different color intensity. Normally, the measurement takes place by color comparison against standard solutions.

The optical-visual colorimetry of weakly colored solutions is, as a rule, carried out in standard cylinders. Such weakly colored solutions occur in many fields of chemical analysis, e.g., in water analysis. The simplest form of the standard cylinder in colorimetry is the Nessler cylinder in which the level of the two solutions to be compared in so varied by pouring out that, seen from above, an identical color impression arises with regard to color shade or color intensity. In the case of the Hehner cylinder, this can be carried out more simply and more exactly by means of a small stopcock for the letting out of the solutions on the lower ends of the cylinders.

Although the principle of the standard cylinder in the optical assessment of weakly colored solutions represents a very simple and sensitive analytical measurement process, in practice it is today used less and less because of the laborious handling. This is to be attributed to the following reasons: the level regulation of the standard cylinder requires time and skill; the standard solution for the color comparison must be prepared daily or very frequently even when only one sample is to be measured, which is often the case, e.g., in the case of control analyses; an inherent coloration or turbidity of the sample solution, which is present in many fields of analysis, cannot be compensated for since the levels usually vary; the standard cylinder can easily be knocked over and requires a flat standing surface which is not present in many potential places of use.

In the case of the optical colorimetry of strongly colored solutions, the brilliance of the color effect of the low liquid columns in the standard cylinder is not sufficient because of strong shadows. Therefore, in the case of solutions with high color density, hitherto transillumination comparators have preferably been used in which the colored solutions are compared with colored synthetic resins or glasses as color standards. When suitable backgrounds, which are as neutral white as possible, are not available for the examination of the transillumination, such comparators can be backed with white cards. Because of the more expensive production, such transillumination comparators are too expensive in reagent equipment sets in which a maximum performance is sought after, having regard to the price.

SUMMARY OF THE INVENTION

The purpose of the present invention is to provide a device and a process with which the described disadvantages are avoided, and to that end there is provided a portable device for the analytical determination of substances in weakly or strongly colored solutions by color development of a sample solution and then comparison thereof with a comparison solution in reagent tubes, in which there is provided a block with at least two openings arranged side-by-side and passing therethrough for the reception of reagent tubes, and a slot passing therethrough for the introduction of a displaceable color table or chart below the reagent tubes; and also a process for the analytical determination of substances in solution by color development of a sample solution and then comparison thereof with a comparison solution in reagent tubes, which is characterized in that the color comparison between two solutions takes place by placing colored reference tables or charts at a right angle below the reagent tubes.

THE DRAWINGS

FIGS. 1 and 2 are perspective views of preferred embodiments of the device.

DETAILED DESCRIPTION

Figure 1:
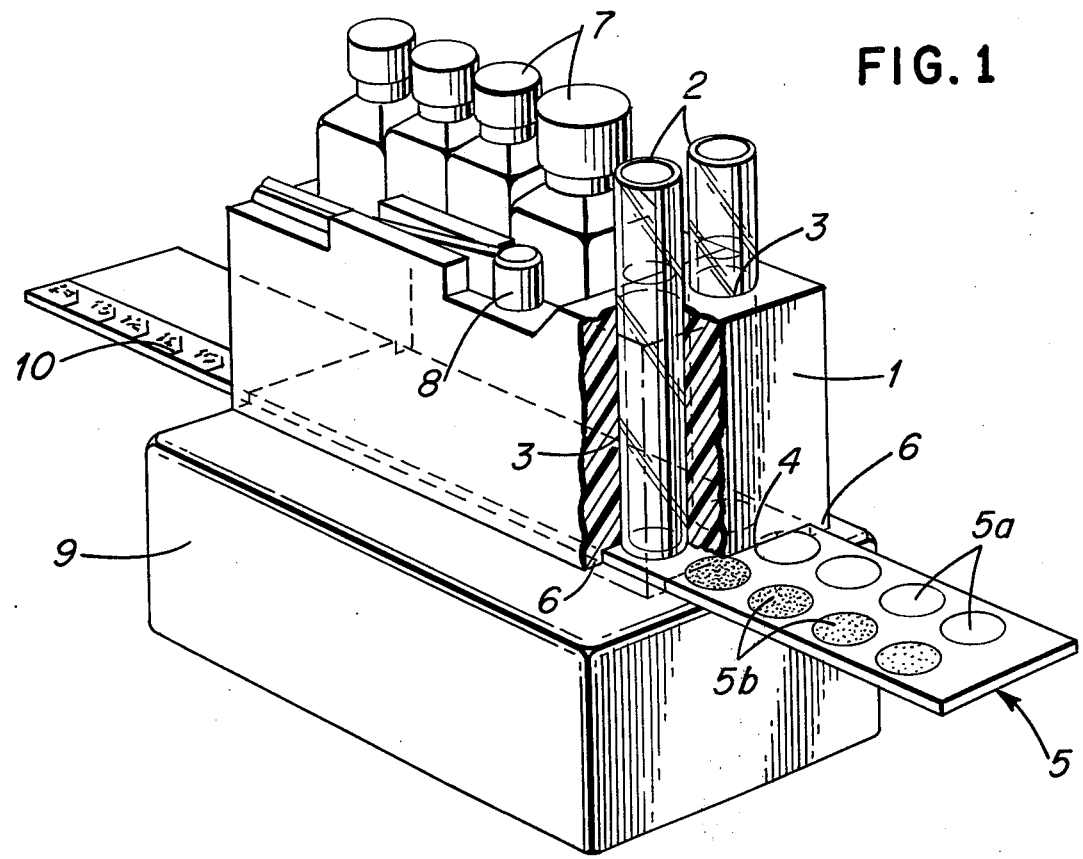

The block 1 is solid and preferably consists of a hard foam material, e.g., polystyrene, which is preferably dark colored to eliminate extraneous lateral light. In this block 1 are provided at least two parallel, vertical, cylinder-shaped openings 3 arranged side-by-side and passing therethrough and into which the two reagent tubes 2 can be introduced. In the case of the reagent tubes 2, these may be inexpensive glasses in the form of test tubes with a diameter of about 2 cm., with flat or rounded bottoms and stopper or screw closures. The glasses preferably lie firmly in the block material; however, they can also be held by cuffs on the glasses, by ribs within the cylinder-shaped openings or by a holding means on the bottom end of the cylinder-shaped openings. The complete slipping through of the glasses can also be prevented by stoppers or screw caps with external projection.

A part of the block 1 or also a separate block belonging to the system can be recessed to receive bottles 7 with the nesessary supply of reagents therein and a measuring spoon 8 for dispensing the reagents. The block stands on a box 9 serving as packaging and also a flat surface.

The slot 4 for the introduction of the color table 5 is preferably formed as a hollow space between two parallel running side pieces 6 on the lower face of the block 1. Reagent tubes 2 with flat bottoms (FIG. 1), which preferably serve for the measurement of weakly colored solutions, are introduced into the block 1 in such a manner that the flat bottom lies directly over the slot 4, i.e., in a plane with the lower side of the block 1. The reagent tubes 2 with rounded bottoms (FIG. 2), preferably serving for the measurement of strongly colored solutions, are, on the other hand, arranged at such a distance above the slot 4 that the focal length of the glass bottom, serving as a convex lens in the case of the filled tube 2, is, as far as possible, not exceeded.

On the basis of the construction of the slot 4, color tables or color discs 5 of the most varied geometry and construction can be pushed below or beside the bottoms of the glasses. In these positions, the color discs 5 can be easily displaced, rotated as well as inserted and taken out. These opaque, non-transparent color discs 5 exclusively reflect the light.

Due to the arrangement and division of the color differences on the color disc 5, it is possible to vary the color below or beside the bottom of the glass with the comparison solution stepwise or continuously, whereas the color below the glass with the sample solution remains constant. In the case of color tables or color discs, these are preferably on rectangular strips of cardboard with the breath of the slot 4 bounded by the side pieces 6. The length of the color tables is not critical and it amounts to about 2 – 5 fold that of the block 1. On the color tables are printed either round colored points with progressive color deepening and paler, preferably white color points or also a continuous color band. The diameter of the colored prints or the breadth of the continuous colored band amounts to about 0.5 – 5 cm., preferably about 2 cm. The color tables are colored or shaded and calibrated for predetermined individual comparison determinations and provided with a scale 10 so that the analysis value can be read off directly on the side of the block 1 opposite to the cylinder-shaped openings 3.

After filling the glasses 2 up to a certain premarked level, the colors of the colored disc 5 appear especially brilliant when seen through the column of liquid. The measure of the brilliance is dependent upon the overhead light, upon the height of the column of liquid, as well as upon the distance of the bottom of the glass from the colored disc 5. In the case of weakly colored solutions, a visually optimally high color saturation is achieved by the direct contact of the bottom of the glass with the colored disc 5. In the case of intensely colored solutions, it is recommended to lift the bottoms of both glasses uniformly above the colored disc 5 so that the colored disc 5, due to the absence of shadow in the case of the lateral incidence of light, appears to be paler through the column of liquid.

Because of the internal reflection of the inner walls of the glasses 2, the brilliance is substantially independent of lateral light influences. For the achievement of an optimum brilliance, the liquid level in the glasses 2 must be equal to or higher than the directly encompassing part of the surface of the block 1. The level of the liquid should preferably project about 1 mm. over the surface of the block 1.

For the carrying out of the analysis, both reagent tubes 2 in the device are filled with water or the sample solution up to a marking of equal height on both glasses 2 which should lie at least 1 mm. above the surface of the block 1. To one of these glasses 2 are added the reagents. After a given time, a color develops in this glass 2, the shade or intensity of which is a concentration measure of the unit to be measured. Should the water or the sample solution have an inherent color or turbidity (optical density), then, as a rule, this is additively superimposed by the coloration brought about.

The colored disc 5 is now pushed under or beside the bottom of the glass, namely, in such a manner that below or beside the glass 2 with the colored solution, a paler, preferably whiter part 5a of the colored disc appears. Beloe or beside the glass bottom of the glass 2 with the untreated water or sample solution lies that part 5b of the colored disc which, by displacement, can pass through a stepwise or continuous color spectrum with the most varied color shades. By means of displacement of the colored disc 5, it is now possible to achieve a position or orientation in which the color shades of the two columns of liquid seen from above appear to be completely or substantially the same. This position or orientation now permits the concentration measure of the unit to be measured to be read off directly on the scale 10 of the colored disc 5.

The effect of the transillumination comparator with neutral white disc placed behind can be achieved by a device according to the invention, which can be produced with low expense. For this purpose, the reagent tubes 2 are arranged at a distance above a reflecting surface, that is, on an overhanging portion 1a of the block (see FIG. 2). The distance between the bottom of the reagent glass and reflecting surface is such that the color impression through the reagent tube 2, seen from above, is not influenced by shadows of the reagent tubes 2 or of the device. Below the reagent tube 2 with the colored solution is present a white or color-tinted reflection surface. On the other hand, below the reagent tube 2 with the comparison solution, there can be provided tables 5 with various color shades. These color shades are to be varied in such a manner that, seen from above, an identical color impression can be achieved in both reagent tubes 2. The different color steps or a continuous colored strip are reproduced on a color scale made of cardboard which, in contradistinction to the relatively expensive transparent colored disc of transillumination comparators, can be produced by simple printing processes.

Figure 2:
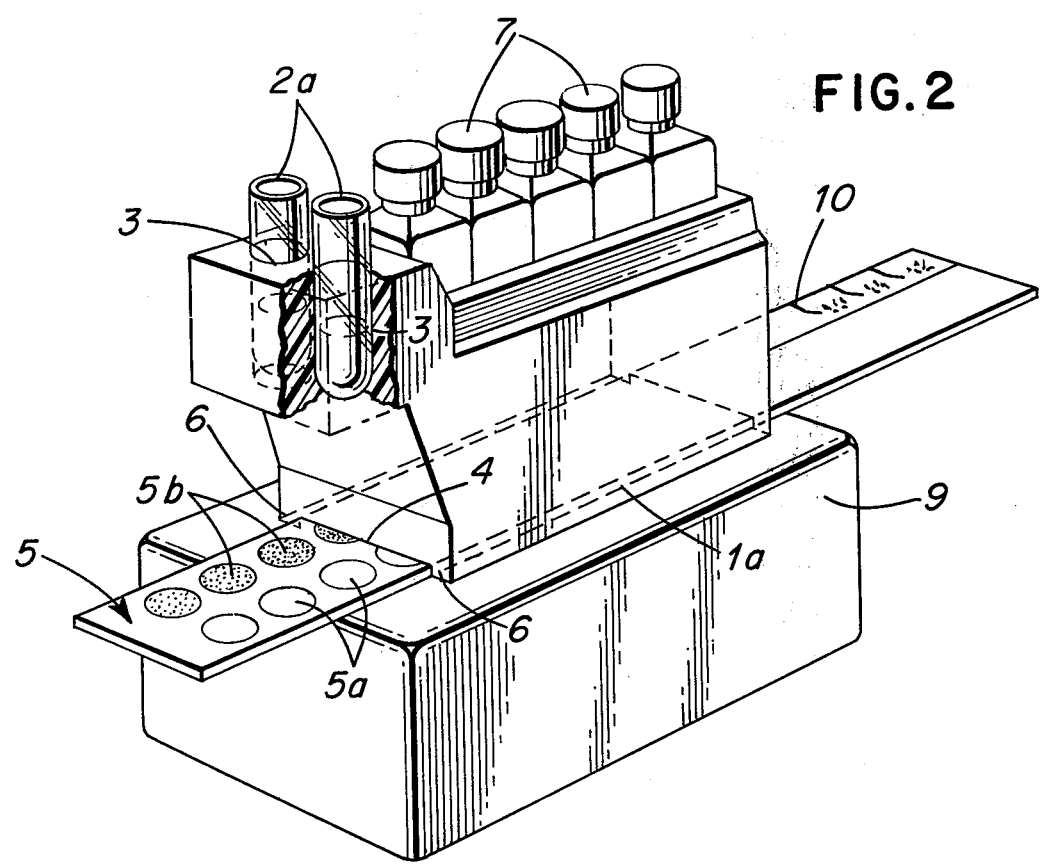

Due to the distance between the bottom of the reagent glass and the colored table 5, normally, due to the reagent glass 2, seen from above, a diminution of the surfaces occurs which appear as points with a diameter of about 0.5 – 5 cm., preferably of about 2 cm. This could necessitate a relative large color scale 5. However, the size of the color scale 5 can be significantly reduced when one uses reagent glasses 2 with round instead of flat bottoms (FIG. 2). In this case, the bottom of the filled glass 2 acts as a magnifying convex lens. When the distance of the bottom of the glass does not exceed the focal distance of this convex lens, seen from above, an enlargement of the color scale 5 is achieved. This permits, e.g., a larger number of colored points to be applied to a color scale of limited size.

With the help of the device according to the invention, the measurement via a subtractive color system is also possible, by means of which the gray or mix-colored shades are produced. A further alternative permits measurements on a turbidometric basis. In this case, below or beside the reagent tube 2 there lies a constantly black or dark background which, seen through a suspension or turbidity, appears to be paler, whereby the lightening represents a measure of the turbidity produced by the reagent addition. Below or beside the comparison column there can be pushed grey or colored tables or discs so that the visible grey or color impression in both cuvettes can be balanced.

The device according to the invention is light and transportable. It is suitable for semi-quantitative analyses at any desired place. Because of the high brilliance of the color systems, a use is possible even in the case of low amounts of light.

I claim:

1. A device for the analytical determination of substances in solution by color development of a sample solution and then comparison thereof with a comparison solution in tubes; and comprising a block formation with at least two tube-shaped openings in generally side-by-side adjacency passing therethrough for reception of solution-containing tubes; means providing a slot along the block traversing the ends of said openings for receiving color tables movable at a right angle relative to the openings.

2. A device according to claim 1, in combination with tubes disposed in the openings and having substantially flat bottoms disposed in close adjacency to the slot.

3. A device according to claim 1, in combination with a color table disposed for movement along the slot.

4. A device according to claim 1, wherein the openings are arranged substantially vertically in the block and the slot is along a lower portion of the block and defined by depending parallel side pieces.

5. A device according to claim 4, wherein the block is substantially opaque to eliminate extraneous lateral light.

6. A device according to claim 3, in combination with tubes disposed in the openings and having rounded bottoms acting as convex lenses disposed above the color table, a distance not greater than the focal length of the lenses.

7. A device as claimed in claim 6, wherein the block is provided with a portion overhanging the color table and in which the tubes are located at the said distance above the color table.

* * * * *